(12) United States Patent
Morken et al.

(10) Patent No.: US 6,533,641 B1
(45) Date of Patent: Mar. 18, 2003

(54) GRINDING ARRANGEMENT AND METHOD FOR REAL-TIME VIEWING OF SAMPLES DURING CROSS-SECTIONING

(75) Inventors: David Bruce Morken, San Jose, CA (US); Russell L. Hudson, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/666,341

(22) Filed: Sep. 21, 2000

(51) Int. Cl.$^7$ ............................................... B24B 49/00
(52) U.S. Cl. ............................ 451/6; 451/285; 451/288
(58) Field of Search ......................... 451/6, 285–288, 451/290

(56) References Cited

U.S. PATENT DOCUMENTS

| | | | |
|---|---|---|---|
| 5,011,280 A | | 4/1991 | Hung |
| 5,067,085 A | * | 11/1991 | Wenzel et al. ................. 451/5 |
| 5,140,776 A | * | 8/1992 | Isdahl et al. ................ 451/429 |
| 5,520,569 A | * | 5/1996 | Endoh ......................... 408/27 |
| 5,726,454 A | | 3/1998 | Chun |
| 5,738,563 A | * | 4/1998 | Shibata ....................... 451/256 |
| 5,741,171 A | * | 4/1998 | Sarfaty et al. ............... 451/287 |
| 5,971,836 A | | 10/1999 | Kogure et al. |
| 6,004,187 A | * | 12/1999 | Nyui et al. .................. 451/285 |
| 6,012,967 A | * | 1/2000 | Satake et al. .................. 451/36 |
| 6,050,876 A | * | 4/2000 | Ouyang et al. .............. 451/254 |
| 6,086,453 A | * | 7/2000 | Fukuoka et al. ................ 451/5 |
| 6,135,854 A | * | 10/2000 | Masumura et al. .......... 451/291 |

FOREIGN PATENT DOCUMENTS

CH          681710 A5      5/1993

* cited by examiner

Primary Examiner—Joseph J. Hail, III
Assistant Examiner—Anthony Ojini

(57) ABSTRACT

Metallographic samples are cross-sectioned to inspect internal features of the samples and to determine the cause of component failures. In order to reach an area of interest that is to be inspected, the cross-sections undergo grinding. Conventional grinding techniques require that a metallographic sample be removed from the grinding apparatus and visually inspected in order to determine whether the area of interest has been reached. An improved grinding apparatus and method of grinding, images the sample while it is being ground so that grinding does not have to be interrupted in order to determine how far grinding has progressed. Real-time monitoring of the grinding process allows precision control of grinding of metallographic samples.

11 Claims, 18 Drawing Sheets

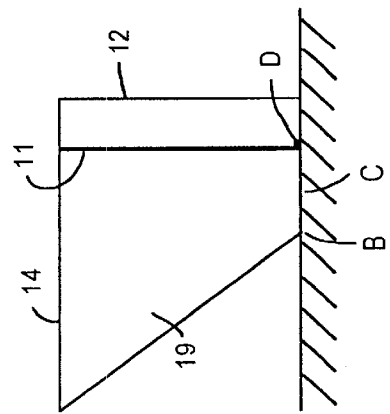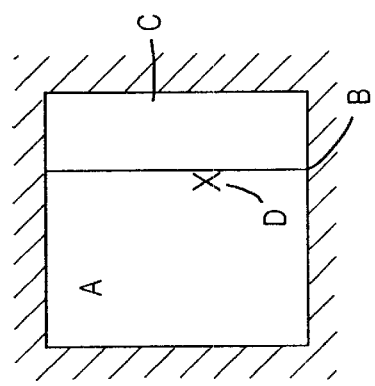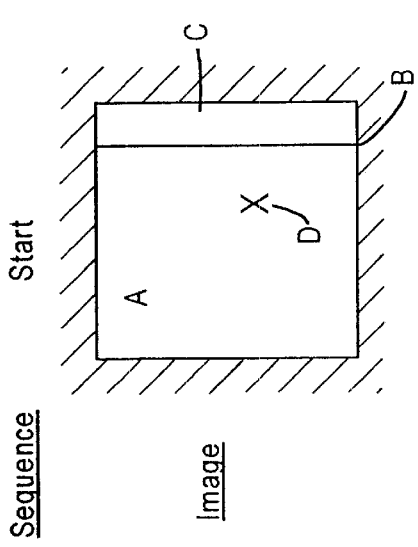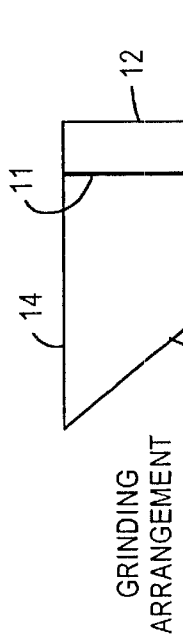
FIG. 14A  FIG. 14B  FIG. 14C  FIG. 14D  FIG. 14E  FIG. 14F

GRINDING ARRANGEMENT AND METHOD FOR REAL-TIME VIEWING OF SAMPLES DURING CROSS-SECTIONING

TECHNICAL FIELD

This invention generally relates to the field of sample preparation for cross-section analysis. More particularly, the present invention pertains to an improved method of preparing a metallographic sample for inspection, by grinding a surface of the sample.

BACKGROUND OF THE INVENTION

The following disclosure describes how the present invention applies to the field of semiconductor devices. However, the invention is not limited to semiconductor device applications, but applies to any sample to be cross-sectioned where an externally observable feature identifies the desired location of the cross-section. Other applications include, but are not limited to metals, ceramics, glass, plastics, composites, etc.

Semiconductor devices comprise a plurality of features formed on a semiconductor wafer. Semiconductor devices typically comprise a plurality of layers made up of conductive and insulative patterns, vias, and trenches. In order to function properly, the semiconductor device layers must be accurately aligned with each other, and sound electrical contacts must be formed with the conductive patterns. Inspections are performed on semiconductor devices as both part of routine quality control, and when trouble shooting to determine the cause of a semiconductor device failure. Because semiconductor devices comprise a plurality of layers, features internal to the semiconductor device are not readily observable by visual inspection. In order to inspect internal features, a cross-section of the semiconductor device is viewed.

Internal features that are inspected include flip chip/package solder bonds, feature and layer thicknesses, microstructure characterization, and the alignment of conductive layers and interconnects and contacts. Possible failure mechanisms that need to be inspected include the presence of voids in welds and solder bonds; layer separation, i.e., delamination or debonding of layers; and misregistration of device features.

The term semiconductor devices as used herein is not be limited to the specifically disclosed embodiments. Semiconductor devices as used herein include a wide variety of electronic devices including flip chips, flip chip/package assemblies, transistors, capacitors, microprocessors, random access memories, etc. In general, semiconductor devices refer to any electrical device comprising semiconductors.

Typically, to inspect the interior of a semiconductor device, a section of the semiconductor device, containing an area of interest that is to be inspected, is cut from the semiconductor device. The section cut from the semiconductor device can be cut using a metallographic saw, such as a wire saw, diamond impregnated blades, silicon carbide blades, or other abrasive saws. A margin of semiconductor device surrounding the area of interest is left after cutting so that the cutting does not damage the area of interest that is to be inspected. The section of the semiconductor device containing the area of interest is often mounted on a suitable holder, such as a stub, which is supported by a chuck. Then the margin surrounding the area of interest is removed by grinding. A grinding wheel or belt with a suitable grinding media is used to grind the sample. As the margin is ground away and the grinding wheel approaches the area of interest, the grinding media is successively changed to a finer grit material. In the final stages of grinding, polishing of the sample is performed. As used in the instant specification and claims the term "grinding" includes polishing.

The section of the semiconductor device being inspected may be mounted on a metallic or plastic stub with either two-sided tape or an adhesive, such as a thermal adhesive. The stub is mounted in a chuck, which supports the sample while it is undergoing grinding.

A sample can also be encased or potted within a transparent polymer resin. When potted, the sample can be held manually or clamped in a sample fixture when grinding.

In the prior art method of grinding semiconductor device samples, the grinding has to be stopped frequently, the sample removed from the chuck, and visually inspected with a microscope to determine whether the area of interest has been reached. The danger exists that grinding can proceed too far and either damage or grind right through the area of interest. The prior art process is inefficient and time consuming because the grinding process has to be interrupted each time the sample is inspected to determine whether grinding is complete.

SUMMARY OF THE INVENTION

There exists a heed in the metallographic sample inspection art to eliminate the problem of over-grinding a sample. There exists a need in this art to perform real-time monitoring of the grinding process to determine how fast grinding is progressing and to determine when the area of interest is reached. There further exists a need in this art to determine when to change the grit media to finer media without having to remove the sample from the chuck and perform a visual inspection of the sample.

These and other needs are met by the embodiments of the present invention, which provide an arrangement for grinding a metallographic sample comprising a metallographic sample, containing an area of interest, with first and second opposing major sides. An imaging arrangement is positioned so as to generate images of the first major side of the semiconductor device sample while the sample is undergoing grinding. A grinding wheel is provided for grinding a surface of the sample.

The earlier stated needs are also met by another embodiment of the instant invention which provides a method of real-time monitoring of the grinding of a metallographic sample comprising: providing a metallographic sample, containing an area of interest, with first and second opposing major sides. The sample is positioned so that a surface approximately normal to the opposing major sides can be ground. An imaging arrangement is positioned to image the first side of the sample while the sample is being ground. A side of the sample approximately normal to the opposing major sides undergoes grinding to approach the area of interest in the semiconductor device. The first side of the sample is imaged while the sample is undergoing grinding to monitor grinding progress.

The earlier stated needs are further met by another embodiment of the instant invention which provides an apparatus for monitoring the grinding of a metallographic sample comprising an imaging arrangement mounted on one surface of a substantially transparent substrate. The imaging arrangement comprises a lens and video camera located along a common optical path with the substantially transparent substrate.

The present invention provides real-time monitoring of the grinding of a metallographic sample by imaging the sample being ground. The imaging arrangement includes a video camera for imaging the sample. In certain embodiments, the substantially transparent substrate provides support for both the imaging arrangement and the sample, and allows the video camera to be positioned away from the grinding area. To prevent damage to the camera, fiber optic tapers, and fiber optic lines comprising fiber optic tubes or cables can be used to further remove the video camera from the grinding area.

To improve image resolution, an artificial light source is used in certain embodiments to illuminate the sample being ground. The light source can either be located in the optical path of the imaging arrangement or it can be a remote light source. The video camera records the image and can either send the output to a video monitor for real-time display or transmit the data to a computer, which captures the image and stores the image data.

Some advantages of the instant invention include the ability to perform real-time monitoring of the grinding process. The sample being ground does not need to be removed and visually inspected to determine how far grinding has progressed. The apparatus and method of the present invention provide a more efficient inspection process. Use of real-time monitoring prevents over-grinding of the sample and the resulting loss of the area of interest. Inspection of metallographic samples is a labor intensive, time-consuming process. The present invention is more efficient because the grinding process is not interrupted to check the sample to see how far grinding has progressed and sample loss because of over-grinding is eliminated.

The foregoing and other features, aspects, and advantages of the present invention will become apparent from the following detailed description of the present invention when taken in conjunction with accompanying drawings.

BRIEF DESCRIPTION OF THE DRAWINGS

FIGS. 14A–14F—depicts the progression of the grinding process and the corresponding images as recorded by the camera.

DETAILED DESCRIPTION

The present invention allows real-time monitoring of metallographic sample grinding. This invention allows the progress of the grinding process to be monitored without having to remove the sample from the grinding assembly and visually inspect the sample under a microscope. This is accomplished by positioning the sample, such as a cross-section of a semiconductor device, in proximity to a grinding surface, such as a grinding wheel. A camera or other optical device is positioned to image a first major side of the sample. An image of the sample is recorded while it is undergoing grinding. The image is displayed on a video monitor or stored in a computer. When an area of interest of the metallographic sample is reached the sample can be removed from the grinding assembly for more detailed inspection. The detailed inspection can include visual, microscopic, or x-ray radiography inspection of the sample.

Figure 1:
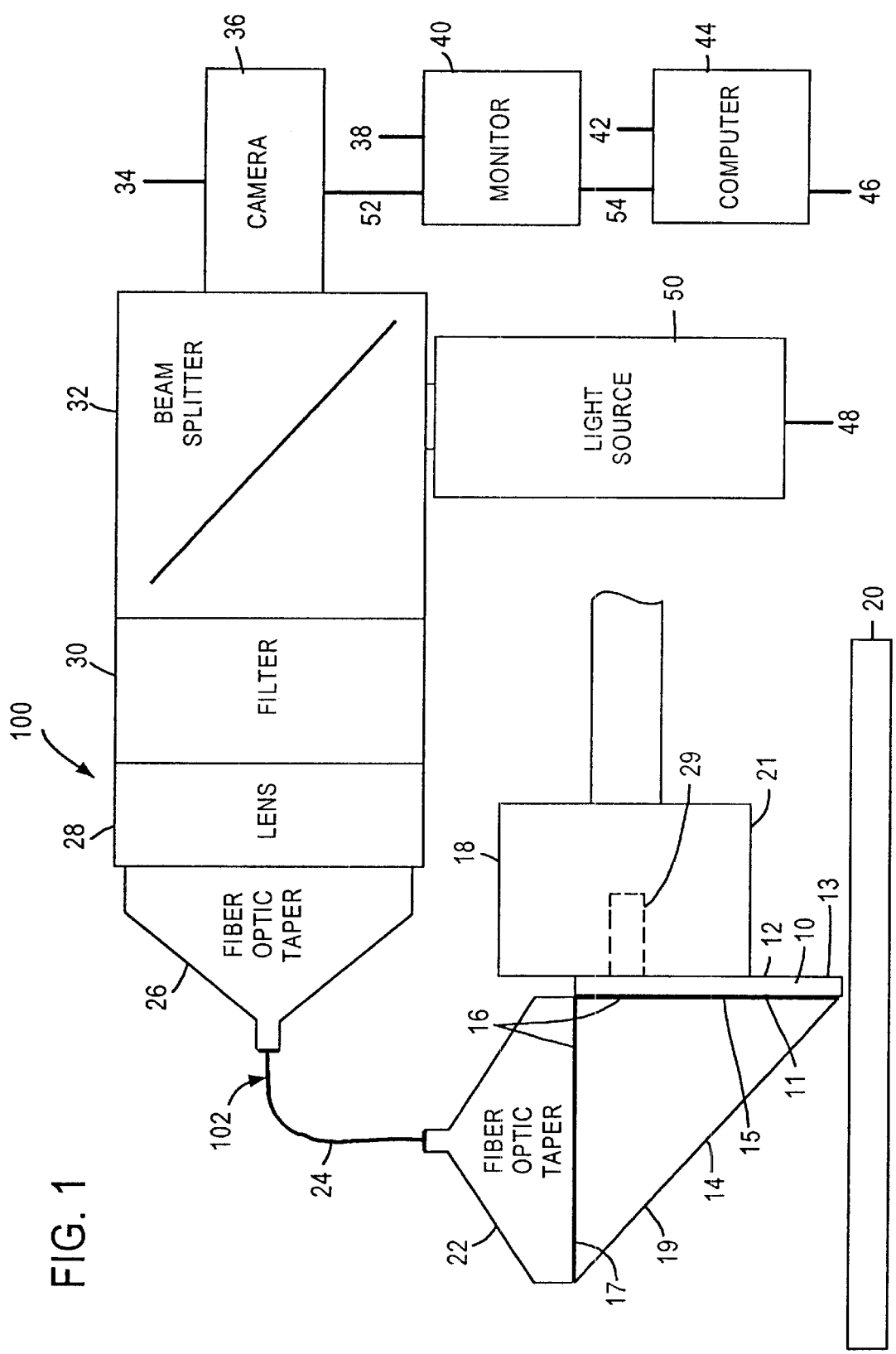
FIG. 1 depicts an embodiment of the present invention where the camera is remote from the grinding area and sample illumination is directed through the optical path of the imaging arrangement.

FIG. 1 shows one embodiment of the present invention. A cross-sectioned metallographic sample 12 is obtained from a larger sample, such as a semiconductor device (not shown). The sample section contains an area of interest 10, which is to be visually inspected. The sample 12 can be cut from the semiconductor device using conventional means, such as a diamond impregnated blade or a wire saw.

Figure 7:
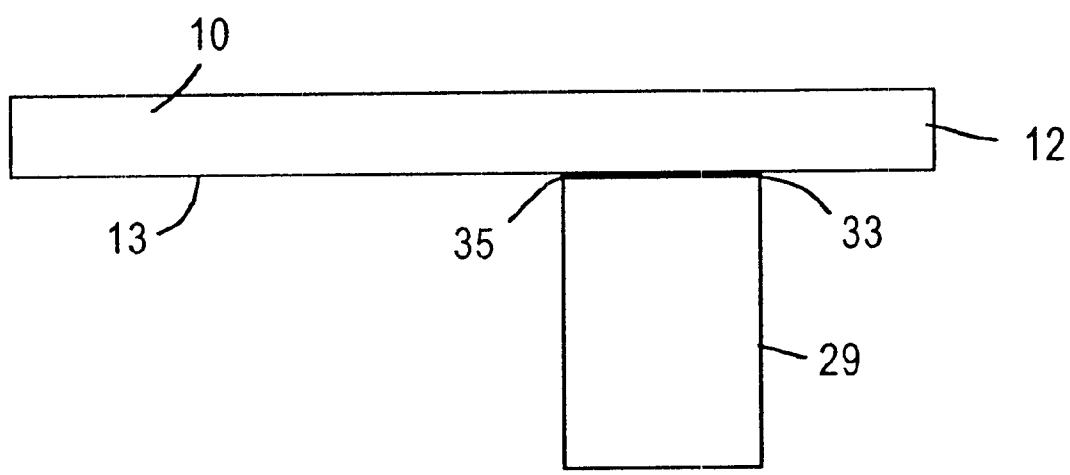
FIG. 7 depicts the sample mounted on a stub.

The sample 12 is securely mounted on a stub 29 using an adhesive 33 such as two-sided tape or a thermal adhesive, as shown in FIG. 7. The stub 29, in turn, is held by a chuck 18. The sample 12 is mounted so that the portion of the sample 12 containing the area of interest 10 extends beyond the edge 21 of chuck 18. Stub 29 typically comprises either aluminum or stainless steel and typically sample 12 rises about 3 millimeters above the stub surface 35.

Figure 16:
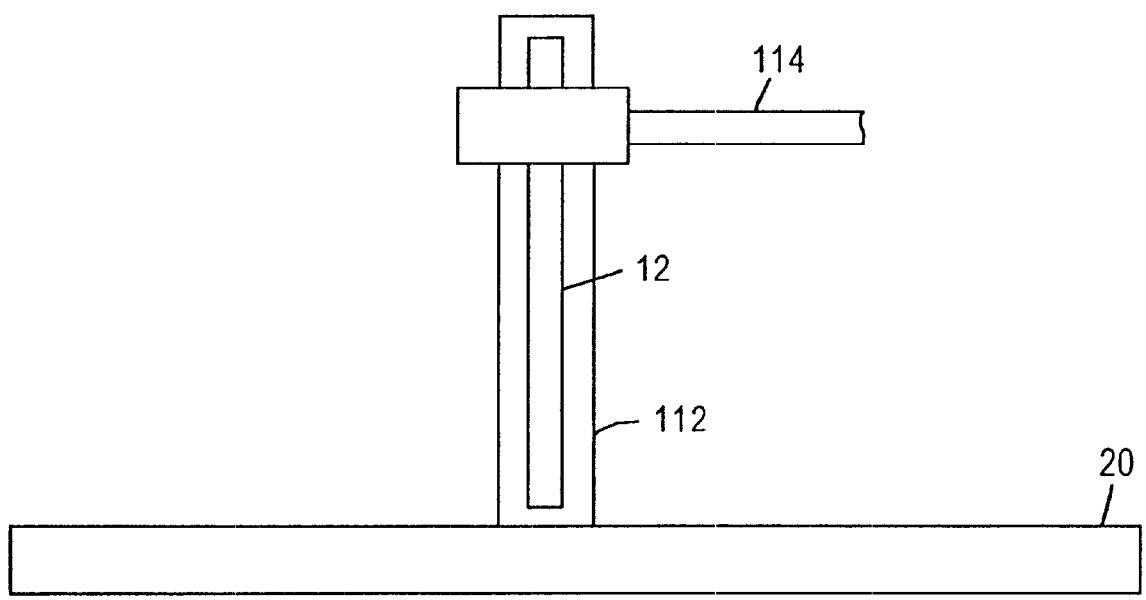
FIG. 16—depicts a clamped sample cast in resin.
Figure 17:
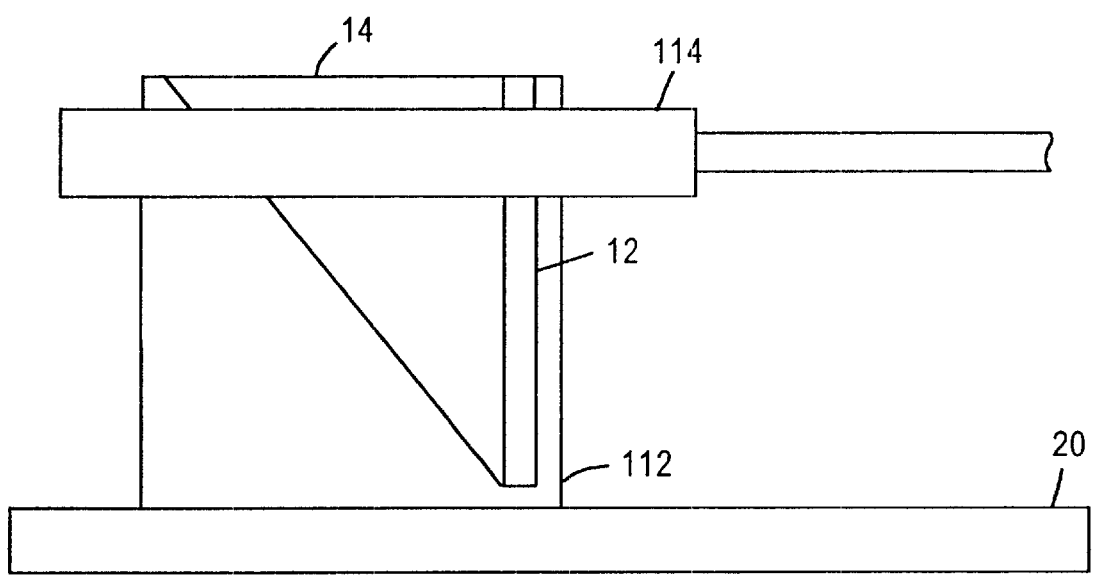
FIG. 17—depicts a clamped sample and prism cast in resin.

The sample 12 can also be securely mounted in a resin, such as an epoxy resin, rather than mounting on a stub. FIG. 16 shows sample 12, cast in a resin 112 and positioned by a clamp 114 against grinding wheel 20. Alternatively, the entire sample 12/prism 14 combination can be cast in resin 112 as shown in FIG. 17.

The sample section contains two major opposing sides. The second side 13 is attached to the stub, while the first side 11 is adhesively attached to one surface 15 of a substantially transparent substrate 14 using an optical adhesive 16. In this embodiment, the substantially transparent substrate is a right angle prism 14. Optical adhesives 16 are commercially available adhesives such as Norland Optical Adhesives available from Edmund Scientific, Barrington, N.J. Optical adhesives are either cured with ultraviolet light or are thermally cured.

The grinding arrangement 100 of the embodiment of FIG. 1 further includes an imaging arrangement 102 which is adhesively mounted using optical adhesive 16 to second surface 17 of prism 14. Prism surface 17 is normal to first surface 15 upon which the sample 12 is mounted. The hypotenuse 19 of the prism forms a reflective surface for reflecting illuminating light onto the first side of the sample 11 and for reflecting the image of sample side 11 to the imaging arrangement 102.

The sample is ground with grinding wheel 20. Initially, the grinding process starts with a relatively course grit grinding media. As grinding progresses and the area of interest 10 is approached the grinding media is successively changed to finer grit grinding media. The final stage of grinding is polishing the sample surface. As used herein, the term grinding includes polishing. Typically, SiC and diamond media is used for rough grinding at the start of the grinding process. For grinding intermediate size features ranging from 30 microns to 0.1 microns, diamond media is used. Diamond grinding media includes diamond paste suspended diamonds, and diamond impregnated sheets. The final stage of grinding, polishing, may be performed with $Al_2O_3$ (alumina) grit. Alumina is used for polishing fine surface features such as those ranging between 1 $\mu$m to 0.05 $\mu$m.

The substantially transparent substrate 14 comprises either a glass or a polymer composition. The polymer composition should be a clear polymer with suitable optical properties. Suitable polymer compositions include acrylic resins and polycarbonate resins.

Prism 14 is commercially available from Edmund Scientific, Barrington, N.J. Prism 14 can either be uncoated or the hypotenuse 19 is aluminized overcoated with inconel and black paint to improve the reflective properties of the prism 14. Although the prism does not need to be metallized, an improved image can be provided by a metallized surface. The prism reflective surface is at an approximate 45° angle to the grinding wheel surface. Prism 14 undergoes grinding at the same time as sample 12. It is desirable to match the grinding rate of prism 14 with the grinding rate of the material of sample 12. Prism 14 is disposable after grinding a sample, so that a subsequent sample to be ground would then be adhered to a new prism.

Figure 8:
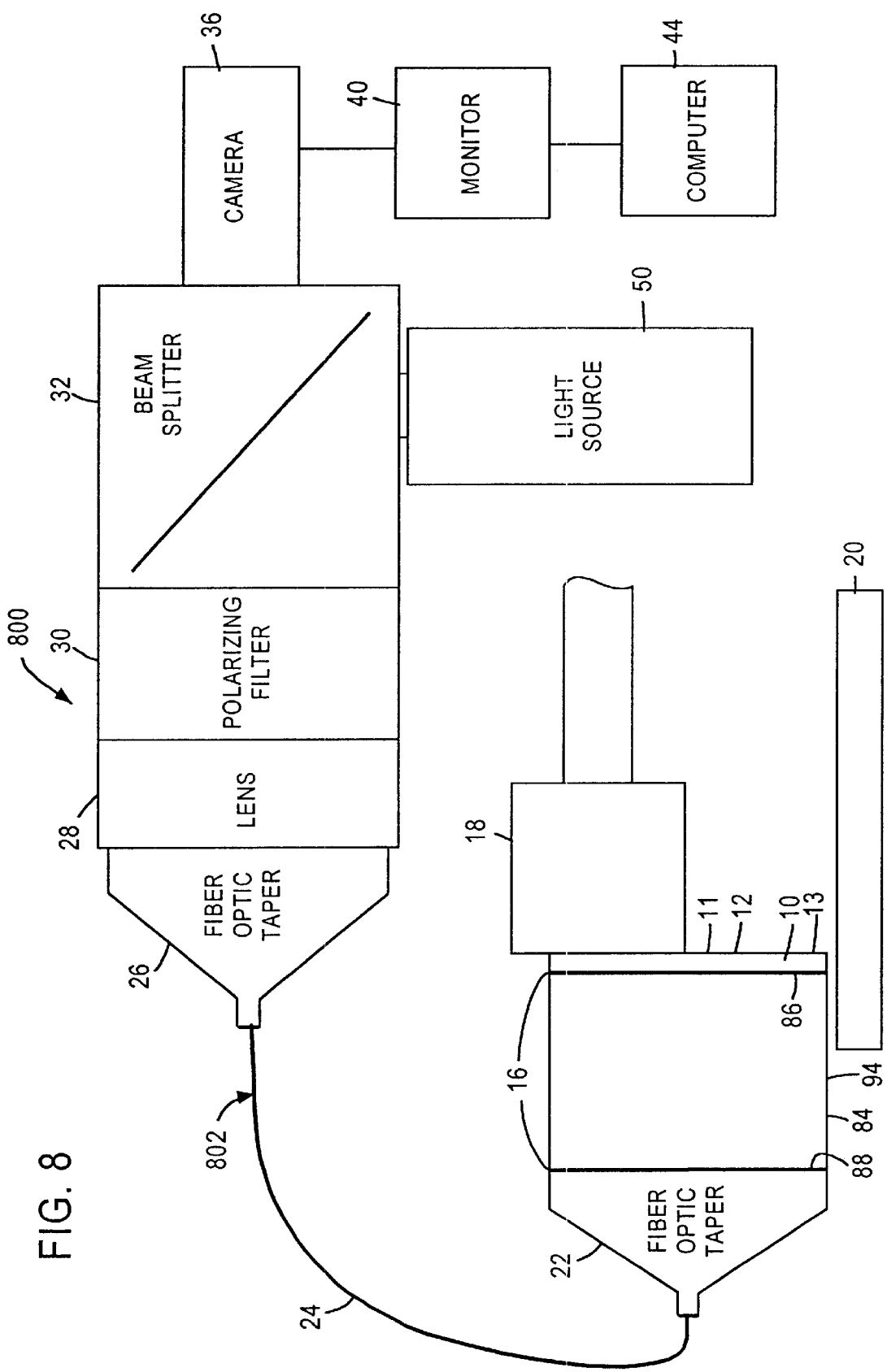
FIG. 8 depicts an embodiment in which the sample and imaging arrangement are attached to a parallelepiped substrate.

In addition to prisms, the substantially transparent substrate is alternatively, substantially a parallelepiped. FIG. 8 illustrates grinding arrangement 800, wherein the sample 12 is attached to a first side 86 of a substantially transparent parallelepiped 84. A fiber optic taper 22 of imaging arrangement 802 is attached to a second side 88 of the parallelepiped 84, directly across from the sample. The image of the first side 11 of sample 12 passes directly through the parallelepiped substrate 84 to the fiber optic taper 22. To prevent damage to the fiber optic taper 22 in this arrangement 800, the grinding wheel 20 grinds only a portion of the lower surface 94 of the substrate 84, not the entire lower surface 94.

After reflecting, off of surface 19, in FIG. 1, the image of sample 12 is directed towards fiber optic taper 22. Fiber optic taper 22 is adhesively attached by means of an optical adhesive 16 to prism surface 17. Fiber optic taper 22 takes a square image from the prism and optically tapers it down to a circular cross-section so that the image can be sent through fiber optic line 24, comprising a fiber optic tube or cable, to fiber optic taper 26 that converts the circular cross-section image back to a square image format, which can be captured by a camera 36. Camera 36 can be a charge coupled device (CCD) or an optical camera. The use of the fiber optic taper 22, 26 and the fiber optic line 24 allows camera 36 to be located at a remote location from the grinding wheel 20. This eliminates difficulties associated with rigidly mounting camera 36. Because the camera 36 is remote from the grinding area the risk of damaging the camera is reduced, and a better, high resolution camera 36 can be used to image the sample 12 instead of a cheaper, lower resolution camera. Fiber optic tapers are commercially available from Edmund Scientific.

Figure 9:
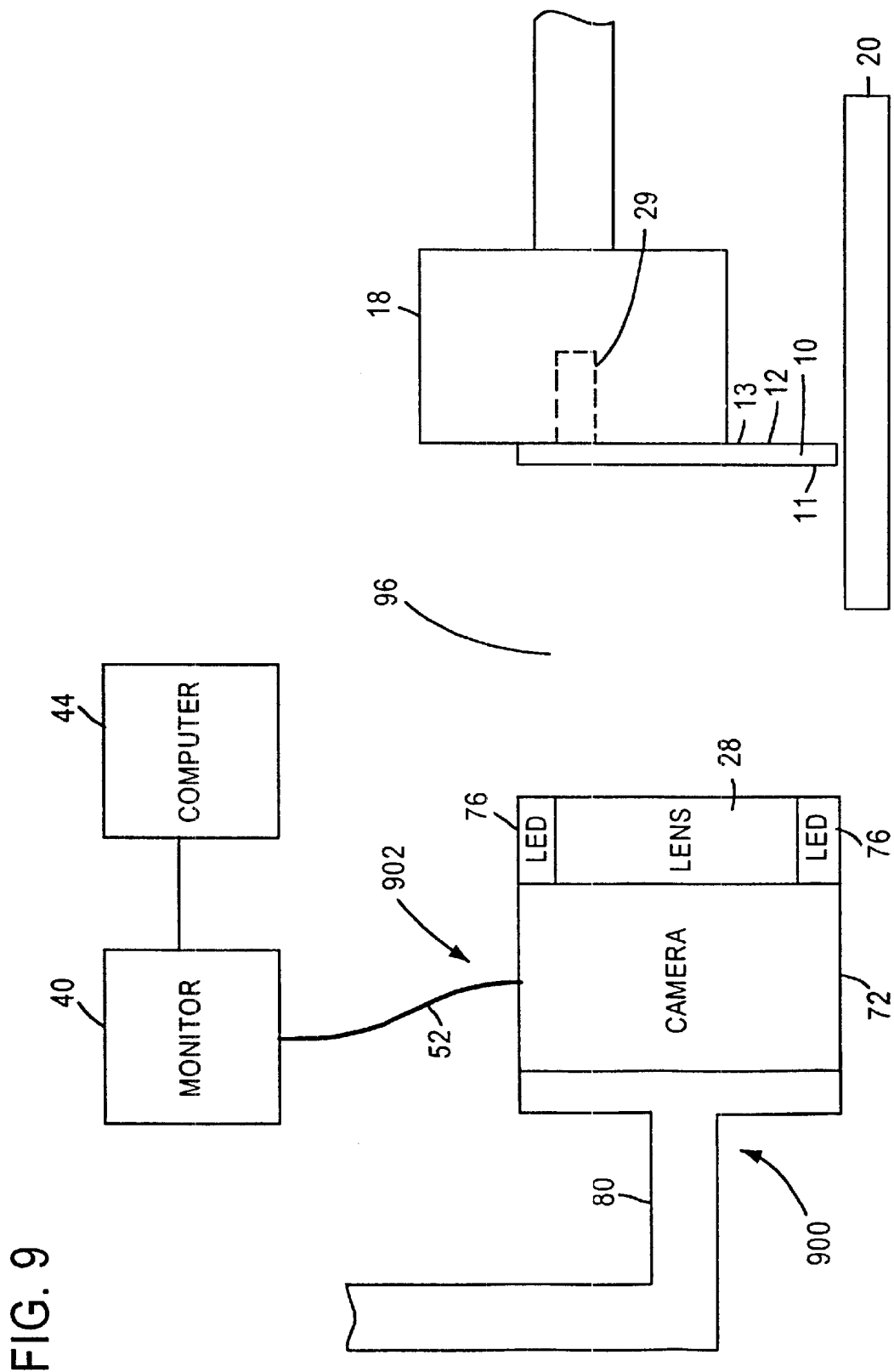
FIG. 9 depicts an embodiment in which the camera is positioned to image the sample across an open space.
Figure 10:
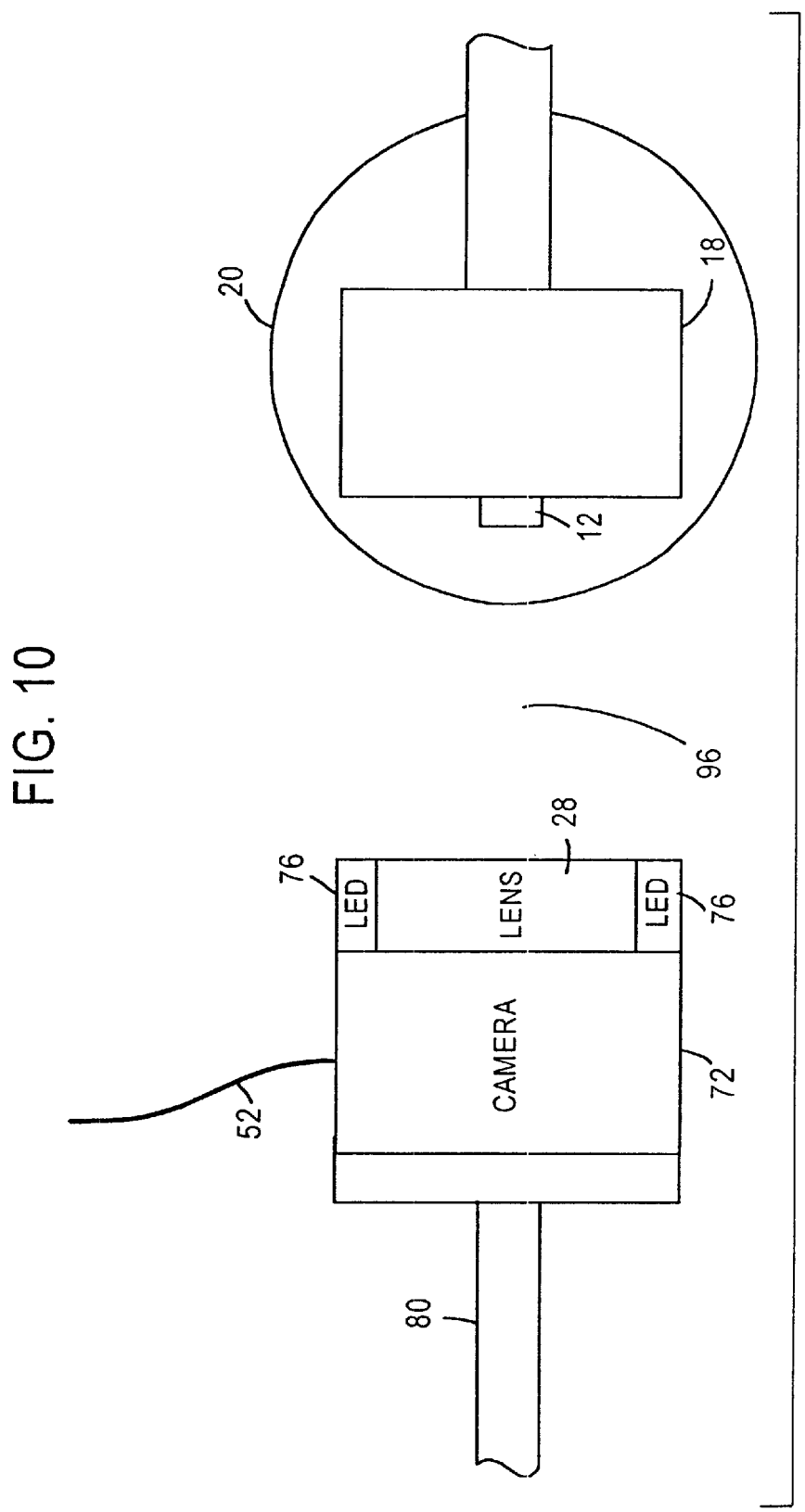
FIG. 10 depicts a top view of an embodiment where the camera is positioned to image the sample across an open space.

In other embodiments, the risk of damaging the camera during the grinding process is reduced by positioning the camera 72 across an open space 96 from the sample 12 and grinding wheel 20. FIGS. 9 and 10 show arrangement 900, wherein imaging arrangement 902 comprises a camera 72 mounted in chuck 80 directly across an open space 96 from sample 12. The image is not obscured by dust generation during grinding, because the lubricants typically applied to the sample during grinding inhibit dust formation. Conventional grinding lubricants include water, diamond grinding paste, and oil.

Figure 11:
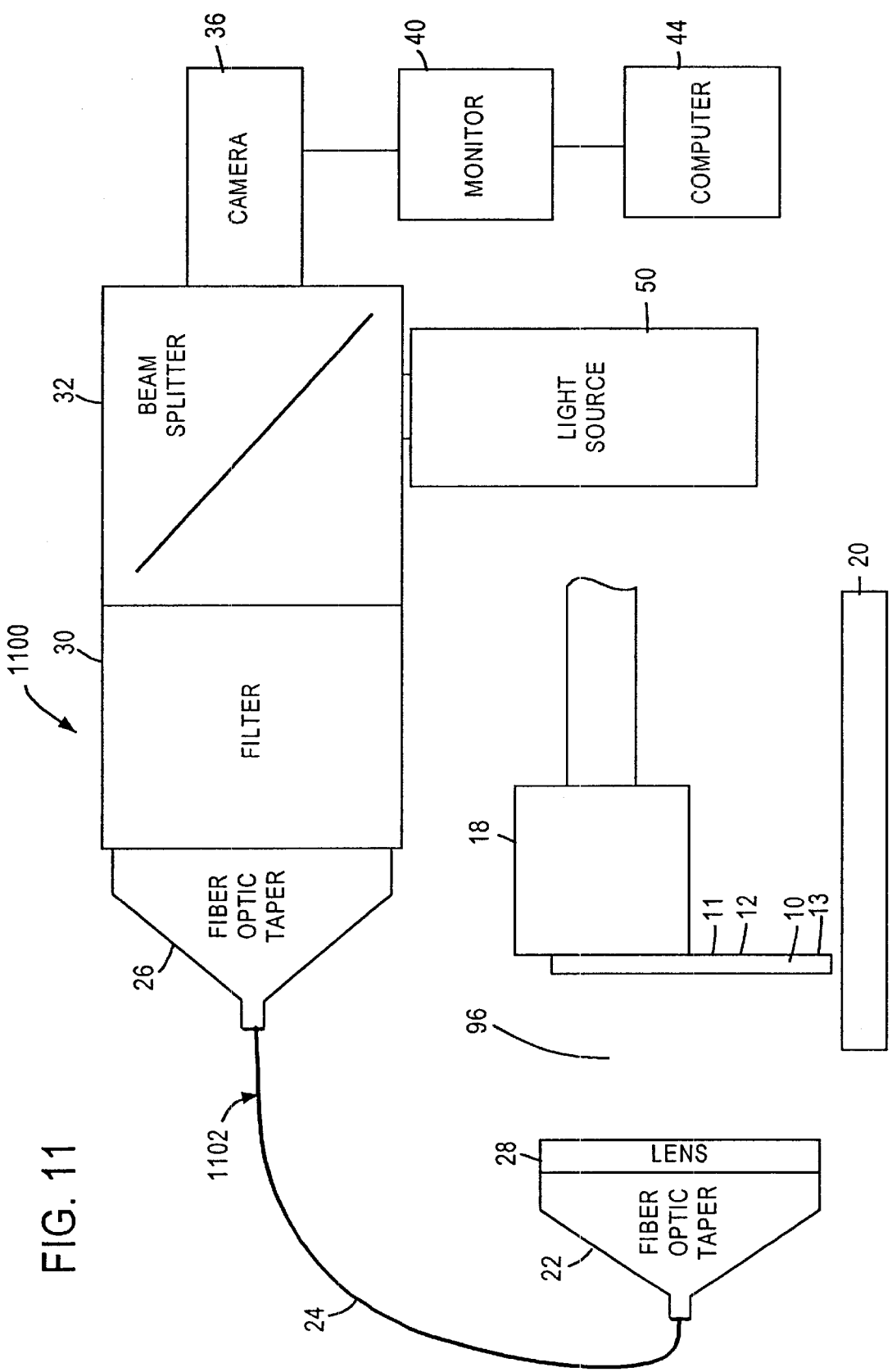
FIG. 11 depicts an embodiment in which a fiber optic taper is positioned across an open space from the sample.

A fiber optic taper 22 and lens 28 can also be positioned directly across an open space 96 from the first major side of the sample to be ground, as shown by arrangement 1100, illustrated in FIG. 11. The fiber optic taper 22 and lens 28 can be positioned using conventional supports (not shown), such as clamps.

As shown in FIG. 1, the image from fiber optic taper 26 is magnified by lens 28, and then the image passes through a filter 30. Filter 30, can be any filter for enhancing the image, including a polarizing filter 30, which reduces reflections and glare.

Beam splitter 32 permits the image to pass through to camera 36 while allowing light from light source 50 to be reflected through the imaging arrangement 102 optical path to the prism 14 and onto the sample 12. The sample 12 can be illuminated with either white light or infrared light.

Camera 36 outputs the image data through the video output 52 to the video monitor 40. The grinding can be viewed in real-time on the video monitor 40. In addition, the video output can be further transmitted through a video output 54 to a computer 44 which captures and stores the video images for later viewing. The video image, if desired, is transmitted to a plurality of computer workstations through a network connection 46. Power lines, 34, 38, 42, and 48 provide power to the camera, video monitor, computer, and light source. The light source 50, video monitor 40, and computer 44 are all conventional, commercially available devices. The camera 36 can be a visible light camera or an infrared camera depending on the source of illumination used. A high-resolution color DSP (digital signal processor) microboard camera, available from Edmund Scientific, is suitable for use in this invention.

Figure 3:
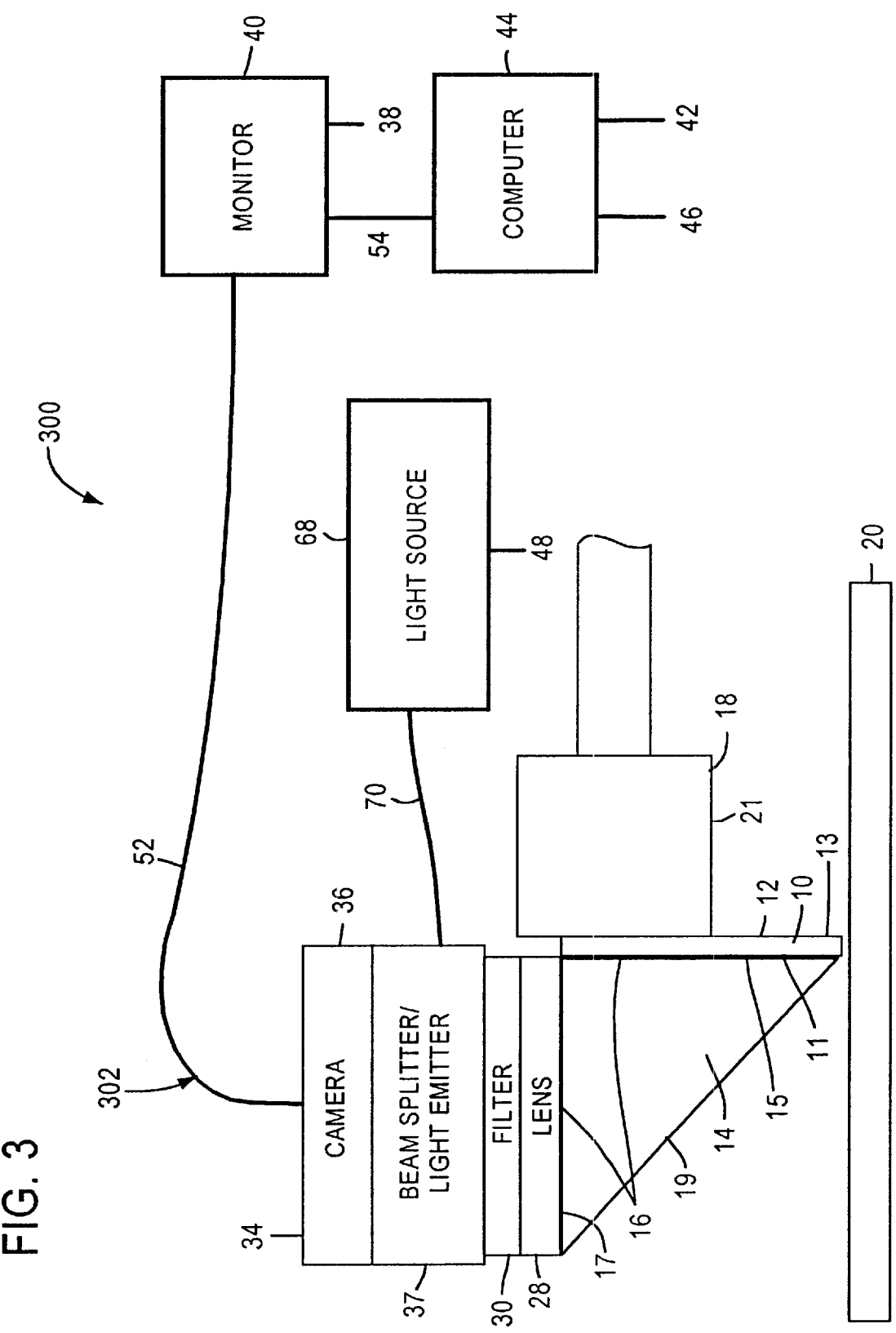
FIG. 3 depicts an embodiment of the present invention where the camera is attached to a prism.

FIG. 3 depicts another embodiment of the present invention. Throughout the figures like reference numbers depict like features. The grinding arrangement 300, comprising optical arrangement 302, is illustrated in FIG. 3. In this embodiment the lens 28, filter 30, and camera 36 are mounted directly on the second surface 17 of prism 14. Light source 68 provides light through fiber optic line 70 to either beam splitter or light emitter 37. The light then passes through a filter 30 and lens 28 and is reflected off the hypotenuse 19 of prism 14 to illuminate the first side 11 of sample 12. An image of sample 12 is then reflected back up through magnifying lens 28 and filter 30 to camera 36. Because camera 36 is attached to prism 14 and is adjacent to the grinding area, a small, relatively inexpensive camera 36 would be suitable for this configuration.

Figure 4:
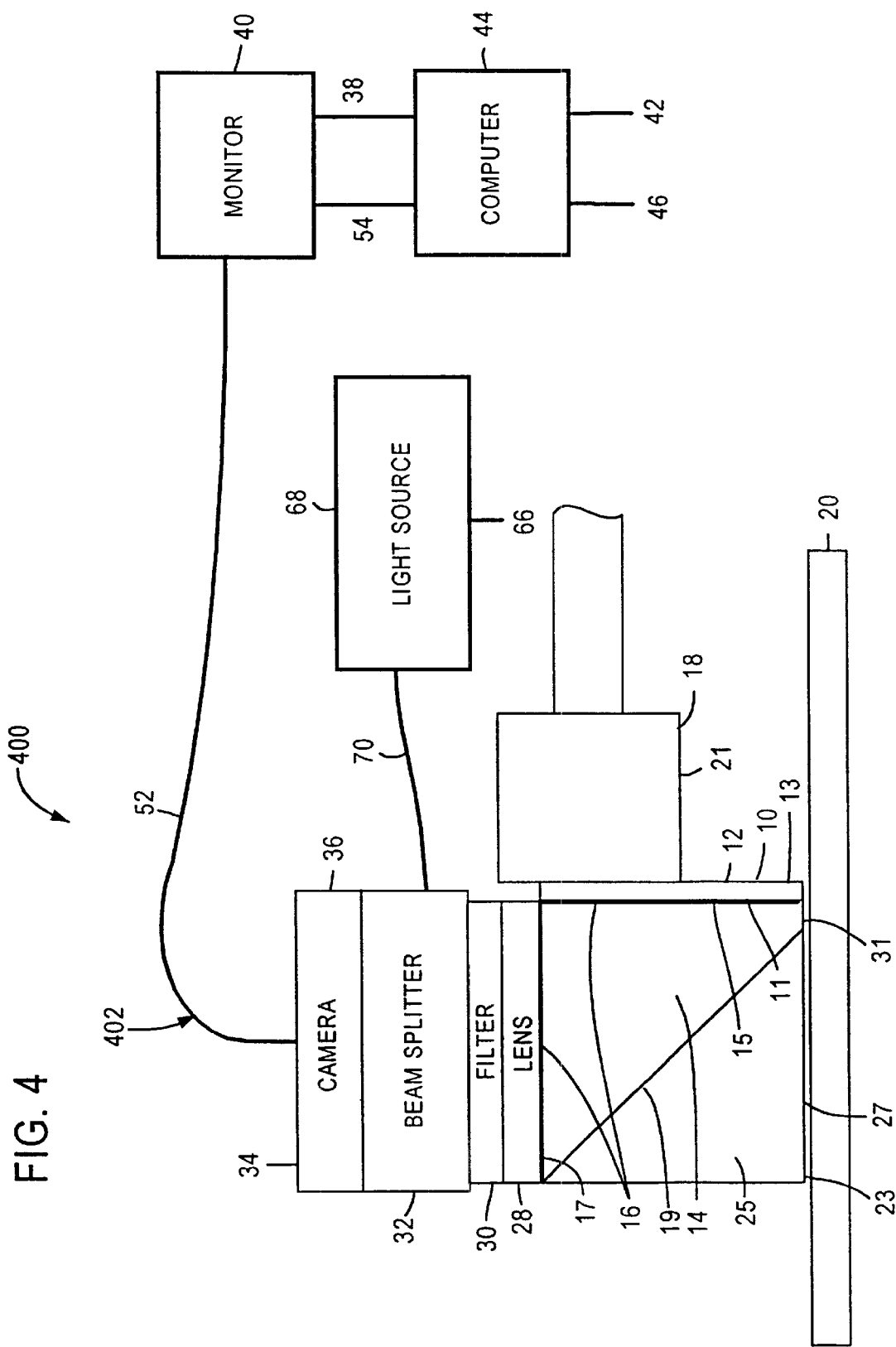
FIG. 4 depicts an embodiment where a dual prism support is provided.

The grinding arrangement 400 depicted in FIG. 4 comprises a dual prism 23 sample support and optical arrangement 402. In this embodiment a second prism 25 is joined with prism 14. The prisms are joined together at their respective hypotenuses 19 to form a parallelepiped. In this embodiment, the dual prism presents a constant surface area grinding surface 27. In the other embodiments, which have one prism, the surface area of the prism/sample increases throughout the grinding process. The constant surface area grinding surface 27 provides for even grinding throughout the grinding process. The two prisms can be attached to each other using the same optical adhesives used to attach a sample to the prism.

An additional improvement is also featured in FIG. 4. First prism 14 has a truncated edge 31 adjacent to the grinding wheel. This truncated edge 31 provides a space between the first side 11 of sample 12 and the reflective surface 19 of the first prism 14 and allows the image at the end of the sample 12 to be reflected nearer to the center of the field of camera 36. This space ensures that the camera records the entire first side 11 of sample 12, and that the end of sample 12 is not outside of the camera's 36 field.

Figure 2:
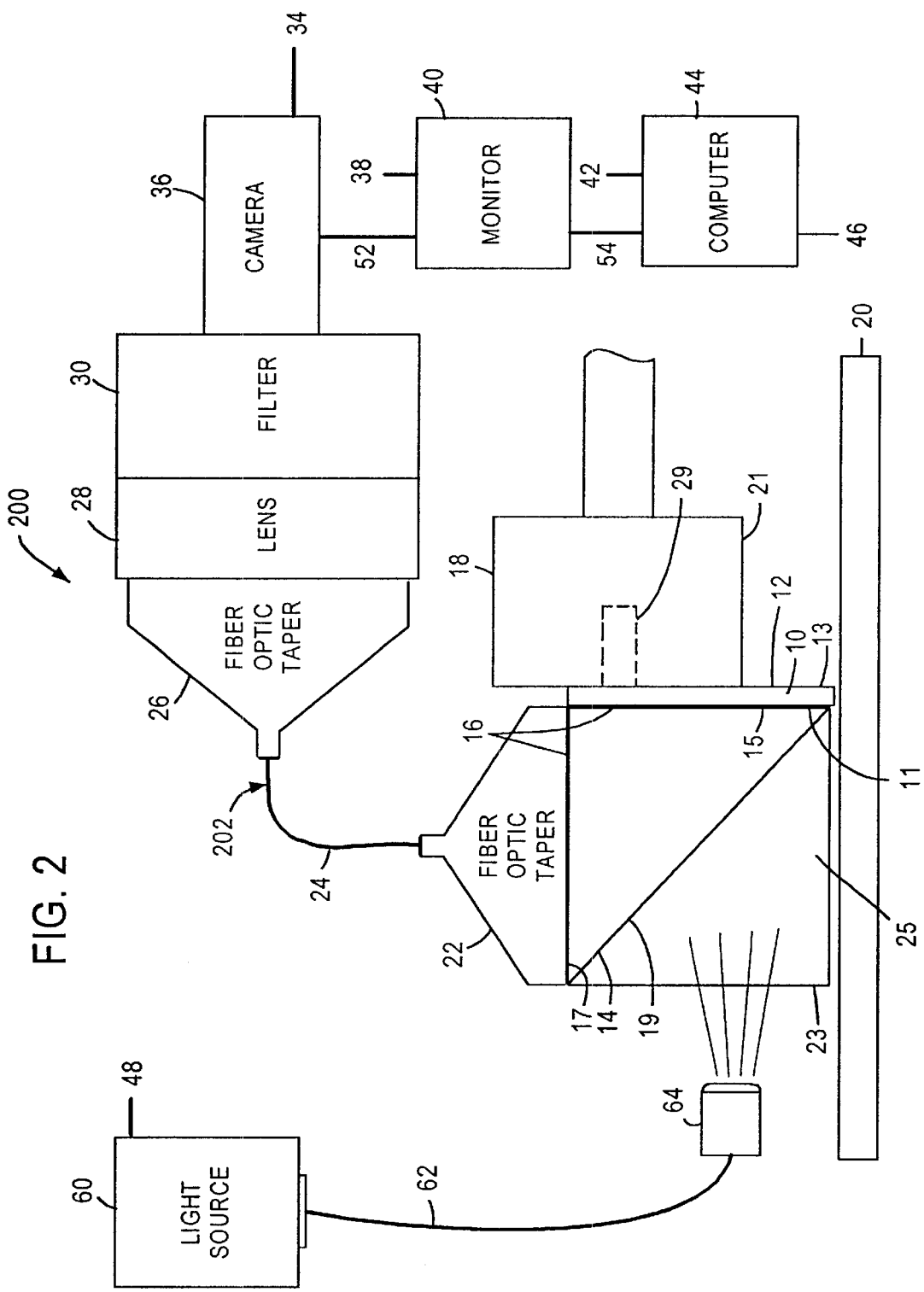
FIG. 2 depicts an embodiment of the present invention where the light source is remote from the optical path of the imaging arrangement.
Figure 12A:
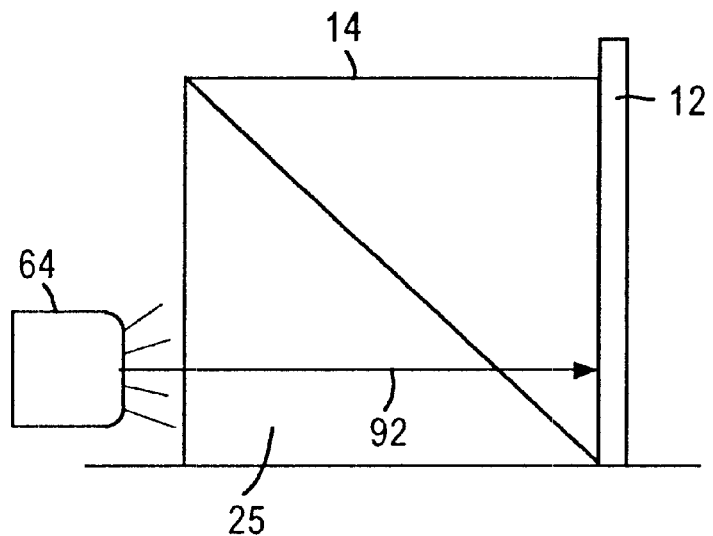
FIGS. 12A and 12B—depicts the effect that a dual prism has on light refraction from an outside light source.
Figure 12B:
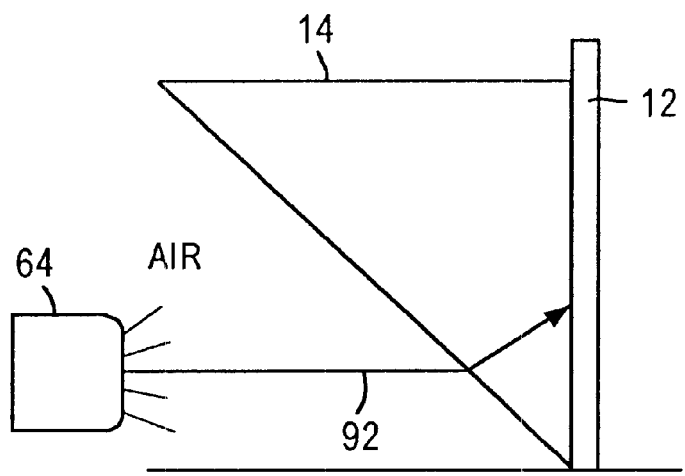

The dual prism arrangement is also useful when an external light source is used, as shown in FIG. 2. In grinding arrangement 200, light source 60 is remote from the optical path of the imaging arrangement 202. Light is transmitted from light source 50 through a fiber optic line 62, comprising a fiber optic tube or cable, to a variable angle or variable rotation lens 64. Lens 64 can be adjusted to provide light at an optimal location or angle. In this embodiment the illuminating light is not transmitted through the optical path and there is no need for a beam splitter. The dual prism 23 prevents the light rays 92 emanating from the lens 64 from being refracted by the hypotenuse 19 of the first prism 14 which could lead to shadows at the position of grinding, as shown in FIGS. 12A and 12B.

Figure 5:
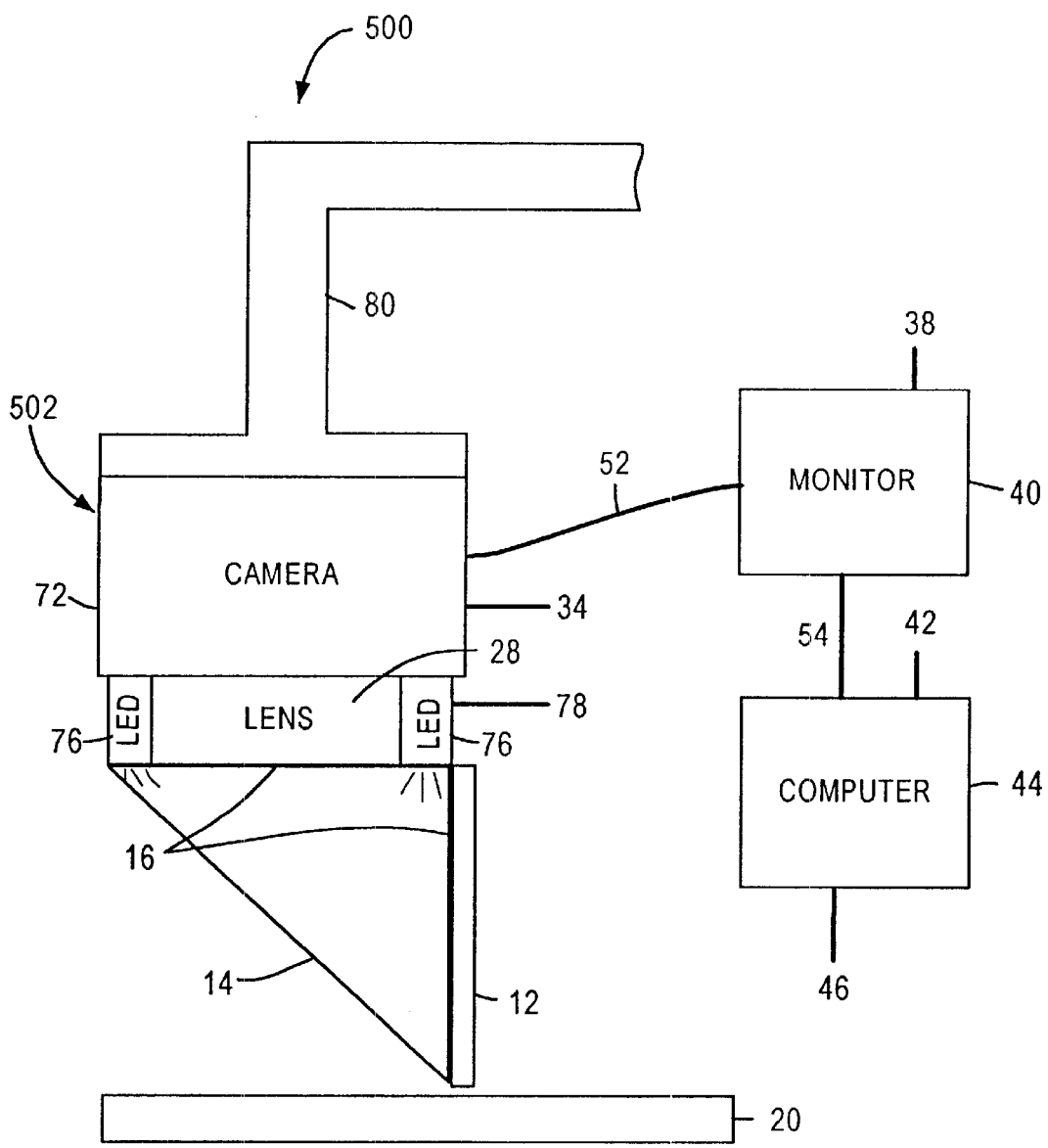
FIG. 5 depicts an embodiment of the present invention where LEDs are used to illuminate the sample and the camera is supported by a chuck.

In alternative embodiments, the camera 72 is held by chuck 80 as shown in FIG. 5. Grinding arrangement 500 utilizes light emitting diodes (LEDs) 76 to illuminate sample 12. In this embodiment, the imaging arrangement 502 comprises camera 72, LEDs 76, and magnifying lens 28. The LEDs are positioned on the outside of magnifying lens 28. The LEDs 76 are powered by power line 78 and comprise either visible or infrared LEDs. Camera 72 is either a visible camera or an infrared camera depending on the choice of LEDs 76. This embodiment provides a compact grinding assembly.

Figure 6:
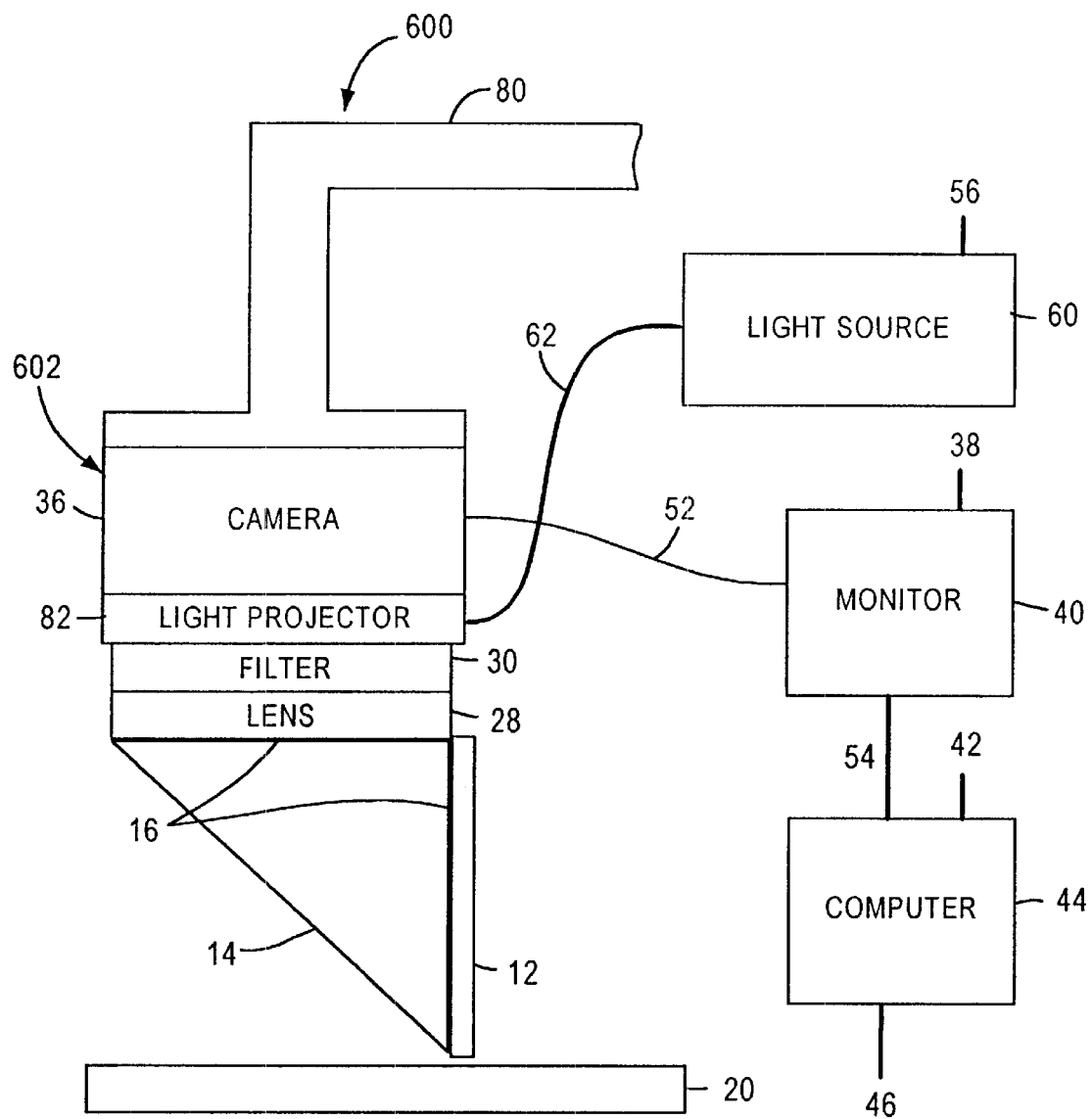
FIG. 6 depicts an embodiment of the present invention in which the camera is supported by a chuck and a light ring is used to illuminate the sample.

In the embodiment illustrated by FIG. 6, the grinding arrangement 600 comprises imaging arrangement 602 wherein the camera 36 is mounted on chuck 80. In this embodiment the light is supplied to the sample 12 by light projector 82. Light projector 82 is an annular shaped light ring which projects light around the outside of the filter 30 and magnifying lens 28. The reflected image from the sample 12 is directed up through magnifying lens 28 and filter 30 through the center of the light ring 82.

Figure 13A:
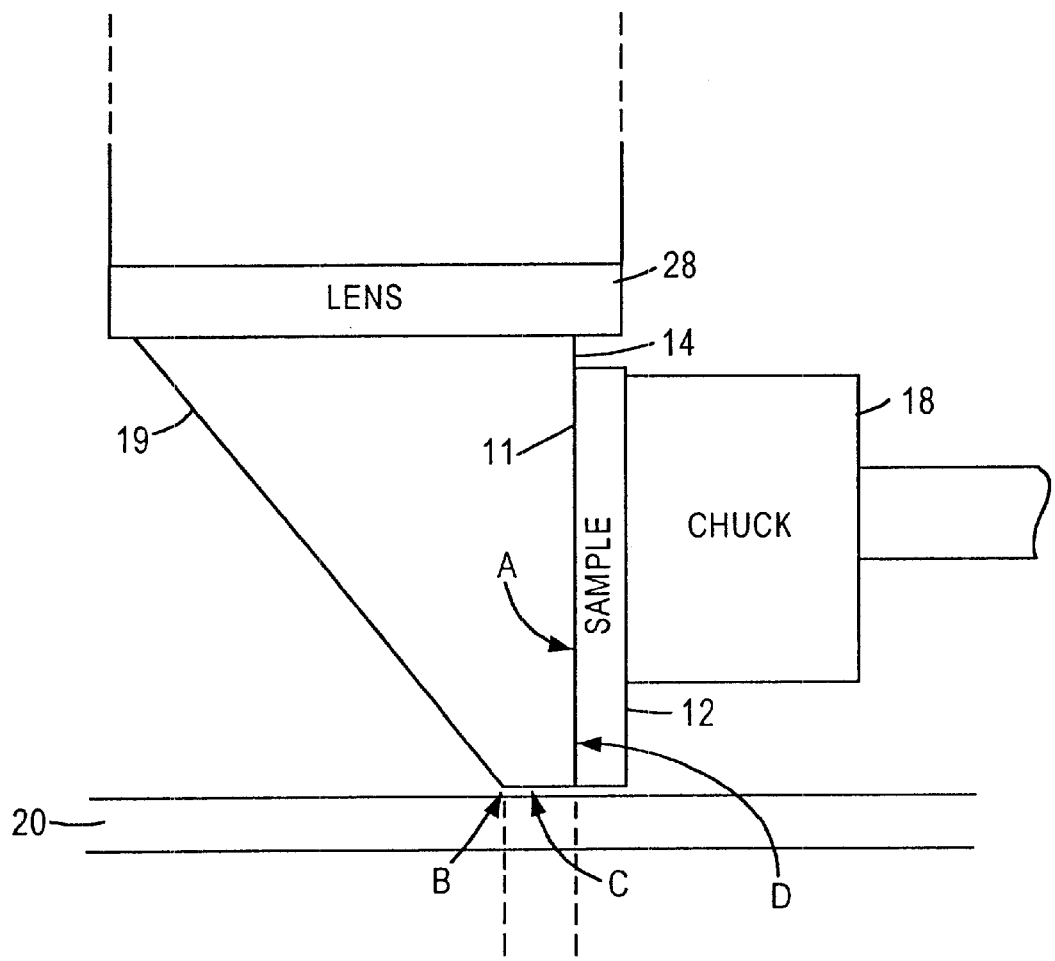
FIGS. 13A and 13B—depicts a detailed view of an embodiment of the invention and the image as recorded by the camera.
Figure 13B:
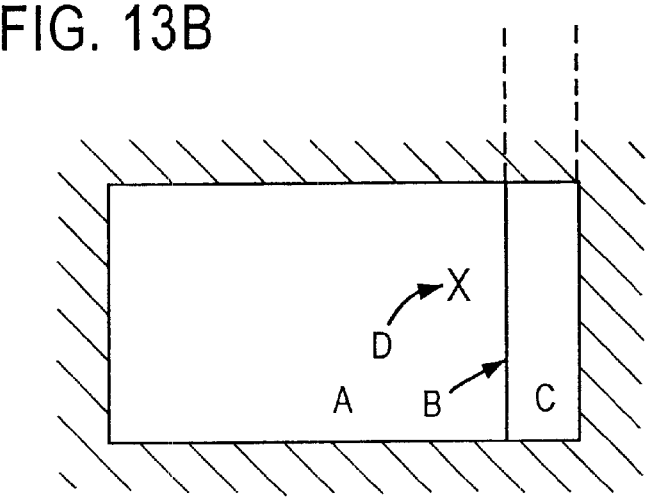

FIGS. 13A and 13B illustrate an example of an embodiment of the invention and an image recorded by the camera. FIG. 13A illustrates a detailed view of an embodiment of the invention. FIG. 13B illustrates the image recorded by the camera of the arrangement in FIG. 13A. Detail A is a view of the face 11 of sample 12. All points of the face 11 are in focus, as each ray of light travels the same distance from the sample face 11, to the reflective surface 19, and up to the camera, through lens 28. B is the edge of the sample 12 being ground. C is the edge of the grinding surface and detail D is the feature of interest.

The progression of grinding is illustrated in FIGS. 14A–14F, which shows a detailed view of the grinding process as feature of interest, detail D, is approached. FIGS. 14B, 14D, and 14F are the images recorded by the camera at grinding stages 14A, 14C, and 14E, respectively. Grinding is completed when B reaches D. As illustrated, the invention allows for continuous, real-time monitoring of the grinding process.

Figure 15A:
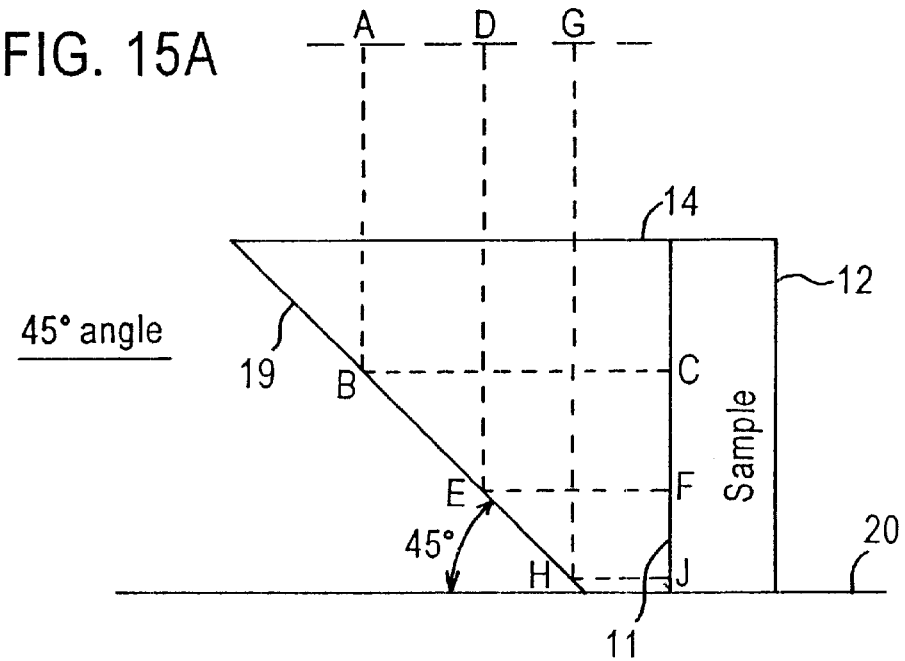
FIGS. 15A–15C—depicts the effect of different prism/grinding wheel angles, and prism/sample angles.

Generally, an isosceles right angle prism is desired in the practice of the invention. As shown in FIG. 15A, the 45° angle of the prism 14 allows the entire face 11 of the sample 12 to be in focus. The lengths of optical paths ABC, DEF, and GHJ are all the same length, so the sample always stays in focus. There is no need to refocus throughout the grinding process.

One of the difficulties encountered with an isosceles right angle prism is that the sample surface 11 near the grinding wheel may become shadowed because of unevenness in the prism surface 31. For example, if the prism 14 grinds at a faster rate than the sample 12, dishing occurs on the prism surface 31. Surface imperfections, such as dishing, distort the sample image as it passes through the prism 14.

Figure 15B:
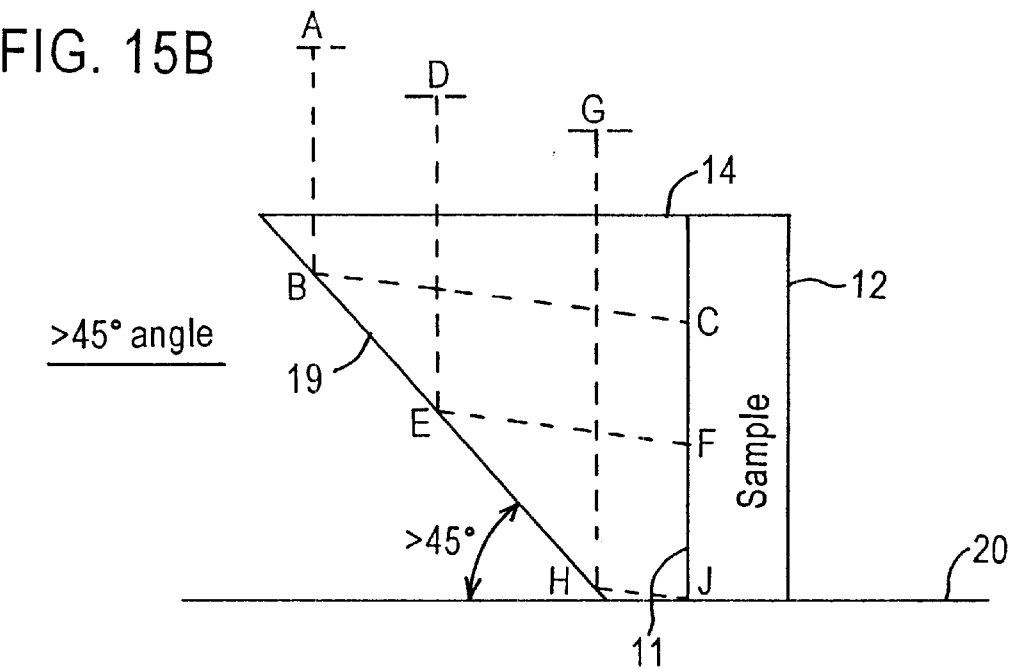

To overcome the limitations of surface imperfections in the prism, a prism 14 can be used that makes an angle with the sample 12 of less than 45°, so that the angle the reflective surface 19 makes with the grinding wheel 20 is greater than 45°. As shown in FIG. 15B, the optical path for point J, at the grinding wheel 20/sample 12 interface, angles upward toward point H, away from any surface imperfections at the prism 14/grinding wheel 20 interface. However, the use of a prism with a reflective surface19/grinding wheel 20 angle of greater than 45° has its own shortcomings. Optical paths ABC, DEF, and GHJ are all different lengths, thus the entire sample surface 11 is not in focus at one time. Refocusing of the optical arrangement is required during grinding.

Figure 15C:
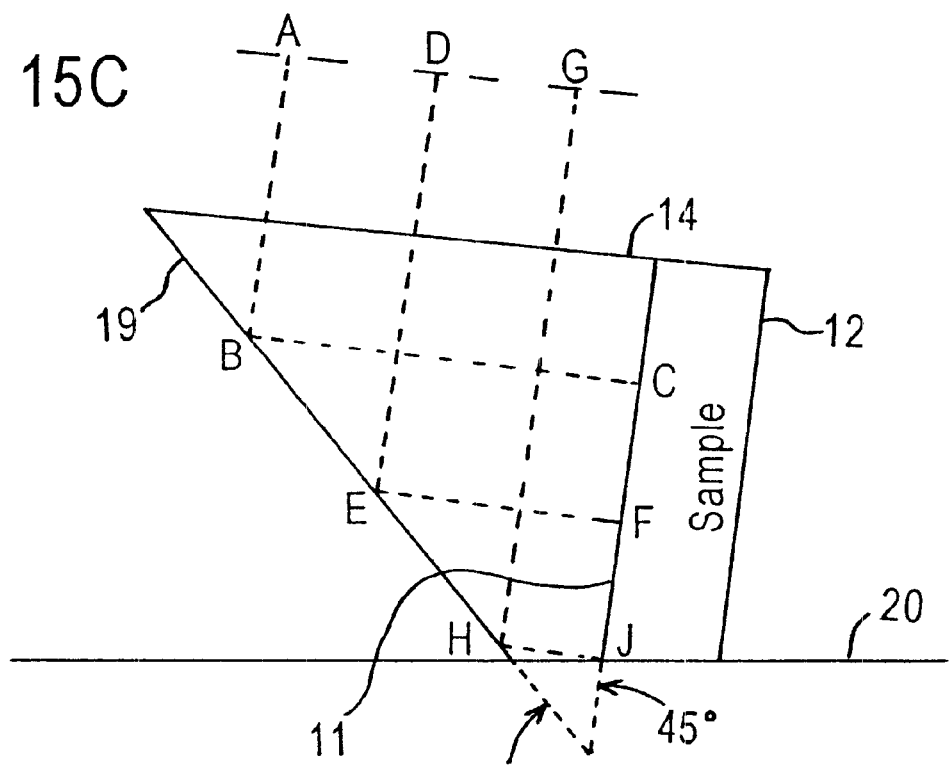

In order to obtain a clear image of the sample 12/grinding wheel 20 interface and to keep the entire sample surface 11 in focus at the same time, an isosceles right angle prism is used and the entire sample/prism/imaging arrangement is tilted with respect to the grinding wheel 20, as shown in FIG. 15C. The imaging arrangement remains approximately perpendicular to the sample surface 11, but is tilted with respect to the grinding wheel 20. Detail J, at the grinding wheel 20/sample 12 interface is not obscured by surface imperfections in either the grinding wheel 20 or prism 14. In this arrangement the entire sample surface 12 is in focus at the camera, as optical paths ABC, DEF, and GHJ are all the same length.

Several embodiments in the invention have been described in the present disclosure. It is understood by one of ordinary skill in the art that other embodiments of the invention are within the scope of the inventive concept as expressed herein. For example the imaging arrangement, in alternative embodiments, is removably adhered to the prism surface. While the prisms are disposable, the lenses, filters, and cameras are reusable.

In order to ensure that the camera and sample are rigidly held in place, in addition to supporting the sample with a chuck, in another embodiment the imaging arrangement, comprising the camera, lens, and filter, are also supported by a support fixture. In other embodiments, a fixture is attached to the second surface of the prism, which contains an opening for the camera lens to fit in. The camera lens can be held in place by a variety of fastening means, including setscrews.

The arrangement for grinding a metallographic sample, the process of real-time monitoring of grinding metallographic samples, and the apparatus for monitoring the grinding of a metallographic sample of the present invention provide an improvement over the prior art grinding apparatuses and methods. Real-time monitoring of the grinding process avoids the time consuming prior art steps of removing the sample from the grinding apparatus and visual inspection with a microscope to determine the state of grinding. The approach of the grinding wheel to the area of interest can be continuously monitored on a video display and the grinding halted once the area of interest is reached. The present invention also prevents over-grinding of the sample. Thus, valuable information about possible failure mechanisms of the semiconductor device is not lost. In addition, technician time is not wasted having to redo quality control inspection tests.

The embodiments illustrated in the instant disclosure are for illustrative purposes only and should not be construed to limit the scope of the claims. As is clear to one of ordinary skill in this art, the instant disclosure encompasses a wide variety of embodiments not specifically illustrated herein.

What is claimed is:

1. An arrangement for grinding a metallographic sample comprising:

a metallographic sample comprising an area of interest, having first and second opposing major sides;

an imaging arrangement positioned so as to generate images of the first major side of the metallographic sample while the sample is undergoing grinding, wherein the first side of the sample is attached to a first surface of a substantially transparent substrate and the imaging arrangement is attached to a second surface of the substantially transparent substrate; and a grinding wheel for grinding a surface of the sample.

2. The arrangement of claim 1, wherein the substantially transparent substrate comprises a material selected from the group consisting of a glass and a polymer composition.

3. The arrangement of claim 2, wherein the substantially transparent substrate is substantially a parallelepiped.

4. The arrangement of claim 2, wherein the substantially transparent substrate is a right angle prism.

5. The arrangement of claim 2, wherein the transparent substrate comprises two right angle prisms, wherein the hypotenuse of one of the prisms abuts the hypotenuse of the other and the two prisms are joined together forming a dual prism parallelepiped.

6. The arrangement of claim 1, wherein a stub is attached to the second major opposing side of the sample, and-the stub is mounted in a chuck.

7. The arrangement of claim 1, wherein the sample is cast in a resin, and the cast sample is positioned for grinding by securing the sample with a clamp.

8. The arrangement of claim 1, wherein the imaging arrangement comprises a lens, filter, and video camera located along a common optical path that includes the substantially transparent substrate and the first side of the sample.

9. The arrangement of claim 8, further comprising a video monitor, for displaying images of the sample, connected to the video camera, and a computer connected to the video camera, for capturing images of the sample.

10. The arrangement of claim 1, further comprising a light source for illuminating the first side of the sample.

11. The arrangement of claim 1, wherein the metallographic sample is a semiconductor device sample.

* * * * *